(12) United States Patent
Van Es et al.

(10) Patent No.: US 11,723,616 B2
(45) Date of Patent: Aug. 15, 2023

(54) METHOD OF VERIFYING A POSITION OF AN INTERVENTIONAL DEVICE

(71) Applicant: CART-TECH B.V., Utrecht (NL)

(72) Inventors: René Van Es, Utrecht (NL); Frebus Jan Van Slochteren, Utrecht (NL); Mathias Meine, Houten (NL)

(73) Assignee: CART-TECH B.V, Utrecht (NL)

( * ) Notice: Subject to any disclaimer, the term of this patent is extended or adjusted under 35 U.S.C. 154(b) by 454 days.

(21) Appl. No.: 16/302,706

(22) PCT Filed: May 18, 2017

(86) PCT No.: PCT/NL2017/050317
§ 371 (c)(1),
(2) Date: Nov. 19, 2018

(87) PCT Pub. No.: WO2017/200385
PCT Pub. Date: Nov. 23, 2017

(65) Prior Publication Data
US 2019/0125289 A1 May 2, 2019

(30) Foreign Application Priority Data

May 19, 2016 (NL) .................................... 2016800

(51) Int. Cl.
*A61B 6/00* (2006.01)
*A61B 6/12* (2006.01)
(Continued)

(52) U.S. Cl.
CPC ............ *A61B 6/5217* (2013.01); *A61B 6/022* (2013.01); *A61B 6/04* (2013.01); *A61B 6/12* (2013.01);
(Continued)

(58) Field of Classification Search
CPC ....... A61B 34/10; A61B 6/4014; A61B 6/022; A61B 6/12; A61B 6/503; A61B 6/542;
(Continued)

(56) References Cited

U.S. PATENT DOCUMENTS

| 2002/0037489 | A1* | 3/2002 | Jones | ................... | A61C 9/0046 |
| | | | | | 433/213 |
| 2004/0015070 | A1* | 1/2004 | Liang | ...................... | G06T 15/08 |
| | | | | | 600/407 |

(Continued)

*Primary Examiner* — Ashley K Buran
*Assistant Examiner* — Helene Bor
(74) *Attorney, Agent, or Firm* — Browdy and Neimark, PLLC

(57) ABSTRACT

A method of providing by a diagnostic medical imaging device, medical image data representing a diagnostic medical image of the tissue of the patient. The method comprises segmenting, using an image segmentation criterion, in the diagnostic medical image data a diseased area image data representing a diseased area of the tissue, defining, in the segmented image data of the diagnostic medical image data, at least one treatment location, identifying, in the diagnostic medial image data, a treatment surface of the tissue, positioning the interventional device to face the treatment surface, determining a normal to a local tangent plane of the treatment surface of the tissue, the local tangent plane facing the treatment location, imaging, by an interventional medical imaging device, at least a part of the interventional device and the treatment location from a first direction perpendicular to the normal to obtain first interventional image data, verifying, using the first interventional image data, a position of the interventional device in a direction of the normal and in a second direction perpendicular to the normal and perpendicular to the first direction, imaging, by the interventional medical imaging system, at least a part of the interventional device and the treatment location from a third direction having a component in the first direction to (Continued)

obtain a second interventional image data, and verifying, using the second interventional image data, a position of the interventional device in the first direction.

41 Claims, 4 Drawing Sheets

(51) Int. Cl.
*G06T 7/00* (2017.01)
*G06T 3/00* (2006.01)
*A61B 6/02* (2006.01)
*A61B 34/10* (2016.01)
*G16H 30/40* (2018.01)
*A61B 6/04* (2006.01)
*A61B 34/20* (2016.01)

(52) U.S. Cl.
CPC ............ *A61B 6/4014* (2013.01); *A61B 6/503* (2013.01); *A61B 6/5235* (2013.01); *A61B 6/5247* (2013.01); *A61B 6/542* (2013.01); *A61B 6/547* (2013.01); *A61B 34/10* (2016.02); *G06T 3/0068* (2013.01); *G06T 7/0012* (2013.01); *G16H 30/40* (2018.01); *A61B 2034/101* (2016.02); *A61B 2034/102* (2016.02); *A61B 2034/105* (2016.02); *A61B 2034/107* (2016.02); *A61B 2034/2051* (2016.02); *A61B 2034/2065* (2016.02)

(58) Field of Classification Search
CPC ... A61B 6/5217; A61B 6/5235; A61B 6/5247; A61B 2034/101; A61B 2034/102; A61B 2034/105; A61B 2034/107; A61B 2034/2051; A61B 2034/2065; A61B 6/04; A61B 6/5211; A61B 6/547; G06T 7/0012; G06T 3/0068; G16H 30/40; G16H 50/20; G16H 50/30

See application file for complete search history.

(56) References Cited

U.S. PATENT DOCUMENTS

| | | | | |
|---|---|---|---|---|
| 2004/0087850 | A1* | 5/2004 | Okerlund | G16H 40/63 600/407 |
| 2008/0123927 | A1* | 5/2008 | Miga | A61B 90/36 382/131 |
| 2008/0198965 | A1* | 8/2008 | Popescu | A61B 6/488 378/19 |
| 2008/0224061 | A1* | 9/2008 | Smith | G01T 1/1647 250/394 |
| 2008/0283771 | A1* | 11/2008 | Li | A61B 6/547 250/459.1 |
| 2009/0274271 | A1* | 11/2009 | Pfister | A61B 6/5229 378/65 |
| 2012/0027278 | A1* | 2/2012 | Chaney | G06T 7/149 382/131 |
| 2012/0183122 | A1* | 7/2012 | Ruijters | A61B 6/504 378/42 |
| 2012/0296196 | A1* | 11/2012 | Boese | A61B 6/487 600/411 |
| 2015/0065855 | A1* | 3/2015 | Van Slochteren | A61B 10/0233 600/411 |
| 2015/0201892 | A1* | 7/2015 | Hummel | A61B 90/37 348/77 |
| 2015/0208948 | A1* | 7/2015 | Wei | A61B 6/50 600/424 |
| 2016/0058399 | A1* | 3/2016 | Narabu | A61B 6/467 600/424 |

* cited by examiner

METHOD OF VERIFYING A POSITION OF AN INTERVENTIONAL DEVICE

The invention relates to a method and software program of verifying a position of an interventional device at a treatment location in a tissue of a patient.

Medical diagnostic and imaging systems are standard equipment in modern healthcare facilities. Such systems provide invaluable tools for identifying, diagnosing and treating physical conditions and greatly reduce the need for surgical diagnostic intervention. In many instances, final diagnosis and treatment proceed only after an attending physician or radiologist has complemented conventional examinations with detailed images of relevant areas and tissues via one or more imaging modalities. Currently a number of techniques exist for medical diagnostic imaging systems. These include magnetic resonance imaging (MRI), computed tomography (CT), X-ray, positron emission tomography (PET), ultrasound and nuclear medicine systems. Other techniques rely on medical signal acquisition. Medical signal acquisition measures electrical phenomena in E.G. heart muscle cells (ECG) or brain cells (EEG). In many instances these techniques complement one another and offer the physician a range of techniques for diagnosing particular types of tissue, organs or physiological systems. Health care institutions often have several such acquisition systems at their disposal, permitting physicians to use the resources as required for specific patient needs. Medical diagnostic systems typically include circuitry for acquiring data and for transforming the data into a useable form which is then processed to create a reconstructed image of features of interest within the patient. The particular components of the systems and the related circuitry however differ greatly between the techniques due to the different physics and data processing requirements. In the current clinical practice diagnostic imaging is performed to assess the patient's disease and the patient's prognosis in order to determine the therapy that needs to be performed. For internal organs like the heart and the blood vessels or the stomach and the intestines the diagnosis and determination of the optimal therapy can be done using medical imaging or medical signal acquisition or via an interventional procedure. Hereby an interventional device (e.g. catheter or endoscope) is inserted into the patient's body and into the organ via a natural body orifice or a small incision to acquire measurements (images, signals, or a tissue specimen) of the local tissue to assess the location and the severity of the disease. With respect to medical imaging, the disease assessment by an interventional procedure may have a different spatial resolution since measurements are performed in only a limited number of locations. An advantage of the use of interventional procedures for diagnosis is that the interventional device can also be used to perform a diagnosis and an intervention, sometimes even during the same procedure. An extension of medical imaging to assess the location and the severity of the disease is the use of Computer Aided Diagnosis (CAD). Hereby the physician is supported by a computer algorithm to assess the presence, severity and the location of the disease. CAD can be performed on both medical images and signals. Another option to determine the optimal therapy is the use of physiological/pathological simulations of the organ to be treated. A simulation model may be based on physiology, medical imaging or medical signals of a patient population or of an individual patient or of a physiology or a pathology. The outcomes of different therapies can be simulated in order to determine the location with the best therapeutic outcomes. The treatment of diseases is done via surgical or minimally invasive techniques. Via these routes therapies like injections, local heating or implantation of stimulation devices can be delivered. During the interventions the surgeon or interventional physician decides upon the characteristics of the therapy (location, type, depth and/or dose) based on visual information of the organ surface (obtained through surgical procedure or biopsy) or images obtained from interventional imaging equipment (minimally invasive). The quantity of the therapy or dose in this respect refers to e.g. the amount of cells with stem cell injections or the amount of energy used for the ablation. The surgeon or the physician uses the information obtained from diagnostic imaging or data acquisition for decision making during therapy.

For the treatment of diseases (pathologies) that have a local focus it is important that treatment is applied at the exact correct three dimensional location with the exact correct quantity. E.G. regenerative therapy, cardiac ablations, or cardiac device implantations need to be targeted to the exact position to obtain the optimal therapeutic results. Evenly important is the determination of the area where the therapy should not be applied to E.G. the area in which the therapy can be harmful since the tissue is too thin and can easily be perforated, or no benefit or even damage is expected based on the anatomical and pathological tissue characteristics. Moreover, to gain the most insight from (pre-) clinical research it is necessary that therapies are standardized as much as possible and targeted in a reproducible fashion to the same location in every subject. The low spatial resolution of the interventional imaging techniques however limits the accuracy to deliver the therapy to the optimal location and makes it impossible to standardize the therapy. Diagnostic medical images or signals allow determination of the optimal location with a high accuracy, but in most cases lack the possibility to visualize the interventional tools. Exceptions are interventional MRI or intravascular ultrasound wherein interventional tools can be visualized in real-time during the scanning procedure. These techniques however have limited applications. When an intervention is to be performed, the interventional device is to be positioned so as to aim at a treatment or delivery site in a body of a patient. In order to position the interventional device, an interventional imaging system may be applied to image the interventional device and a relevant part of the body of the patient. As an interventional imaging system commonly provides a two dimensional image, an iterative imaging and position adjustment technique is commonly applied, whereby the interventional imaging system provides images from various incident angles, while 3 dimensional position adjustments of the interventional device may be performed in between the subsequent imaging procedures. As multiple interventional images are usually taken, the load (e.g. an X-ray radiation load) for the patient may be relatively high.

A first aspect of the invention intends to provide an accurate positioning of the interventional device while allowing to keep a number of interventional images low.

According to a first aspect of the invention, there is provided a method of verifying a position of an interventional device at a treatment location in a tissue of a patient, the method comprising:

receiving from a diagnostic medical imaging device, diagnostic medical image data representing a diagnostic medical image of the tissue of the patient;

segmenting, using an image segmentation criterion, in the diagnostic medical image data a diseased area image data representing a diseased area of the tissue;

defining, in the segmented diagnostic medical image data, a treatment surface of the tissue;

projecting the diseased area, represented by the diseased area image data, onto the treatment surface;

defining a treatment location on the treatment surface, the treatment location being in, out or at a boundary of the diseased area projected onto the treatment surface;

registering data representing the treatment surface and the treatment location at an interventional imaging device;

determining a first direction perpendicular to a normal to a local tangent plane of the treatment surface of the tissue, the local tangent plane being located at the treatment location on the treatment surface;

after the interventional device has been positioned to face the treatment location on the treatment surface (e.g. positioned adjacent to the treatment location on the treatment surface), performing the steps of:

imaging, by the interventional medical imaging device, the tissue at the treatment location and at least a neighbouring part of the interventional device to obtain first interventional image data from the first direction;

enhancing, using the first interventional image data, a position of the interventional device in a direction of the normal and in a second direction perpendicular to the normal and perpendicular to the first direction.

Accordingly, first, a medical image is taken by a diagnostic medical imaging device. The diagnostic medical imaging device may be a CT, MRI, SPECT, PET, Ultrasound or any other medical imaging device. The medical image may be a two dimensional image, a sequence of 2 dimensional images, each spaced apart in a third dimension perpendicular to the 2 dimensions of the images, so as to provide 3 dimensional information, or a 3 dimensional image. Also, a 2 or 3 dimensional image may have been taken as described above, at different time instances, whereby the images are combined into a 4 dimensional (3D+time) image. The image may be an image of any suitable tissue of the patient, e.g. any suitable organ, such as a heart, lung, liver, etc. or a tumor.

In the image, the tissue of the organ of interest is segmented so that at least one of the segmentation borders forms a continuous surface where the therapy can be applied to. This is hereafter referred to as the treatment surface. The treatment surface may form a factual surface of the organ (a surface where therapy may be applied, such as an internal surface or external surface of the organ), or may form a surface within the tissue itself. The treatment surface may be formed by a curved surface which extends in a 3 dimensional space. This organ segmentation can be done automatically when a clear image contrast exist between the tissue of the image and the surrounding tissue. Alternatively manual correction of the organ segmentation is done, or the organ segmentation is done completely manually. The medical image in combination with the organ segmentation is used as an input for a quantification algorithm to determine tissue regions with a particular degree of a pathology or another tissue or organ characteristic. The quantification determines the local degree of the affected and applicable tissue characteristic in the organ of interest.

Methods to quantify local tissue characteristics and use it as an input for automated calculation of therapy locations can be subdivided into methods based on differences that are perceptible on the tissue level, or differences that are perceptible on the organ level or can be based on external parameters.

Tissue Level

Image techniques that provide a local difference on the tissue level are amongst others and not limited to:
1. fibrosis imaging via contrast enhancement or via mapping of relaxation parameters by MRI mapping techniques
2. perfusion imaging via contrast hyper enhancement of well perfused tissue and lower enhancement of tissue with a low perfusion
3. deformation imaging via the analysis of motion datasets wherein the displacement of the tissue is mapped and used to calculate tissue deformation
4. timing maps composed through an analysis of time dependent processes like deformation or electrical activation
5. wall thickness via the measurement of the local tissue thickness
6. stiffness via the propagation velocity of a pressure wave in the tissue
7. calcium imaging to visualize the calcification of blood vessels Organ Level Image techniques that provide a local difference on the organ level are amongst others and not limited to:
1. local organ shape/curvature via the measurement of the local geometry of the organ
2. local wall stress via the analysis of internal tissue or organ pressure in combination with the normal local tissue thickness and local organ shape
3. local reachability by the interventional device via the analysis of the organs geometry in combination with the technical specification of the interventional device External External inputs for the calculation of the optimal therapy location are amongst others and not limited to:
1. The distance to other organs that are sensitive for interaction/interference with the planned therapy
2. Expert input that is either or not taken from a knowledge database and can be used to include or exclude certain locations for treatment
3. Input from a (e.g. patient specific) simulation model to predict the relation of the treatment to the outcome All characteristics on the organ and tissue level and input from external sources may serve as an input for treatment planning.

The result of the organ segmentation process is a two or three dimensional spatial object representing at least the treatment surface of the organ of interest. The anatomy, pathology or other tissue or organ characteristic that is used for treatment planning is processed using a specific technique for each parameter. Techniques used are the automatic or manual segmentation of the organ and specific areas within the organ, or result from the analysis of specific characteristics within the segmented organ or the unsegmented medical image. The resulting disease presence or severity is reconstructed into a two or three dimensional spatial object. Both the treatment surface and the diseased area are now positioned with respect to each other in an anatomical correct orientation, and the disease presence or severity is projected onto the treatment surface using a radial projection technique.

The radial projection algorithm divides the organ (e.g. in this case the left ventricle of the heart) into an finite number of equally spaced segments that are oriented perpendicular to the treatment surface at the intersection point of the treatment surface and the projection line. The intersection points are located at the vertices of the treatment surface mesh. To project the parameter of interest on top of the endocardial treatment surface three types of projections can occur:

1) Projection of the presence or absence of the disease.
   A binary 1 is projected onto the treatment surface when the diseased area is crossed by a projection line. (E.G. fibrosis imaging)
2) Projection of pixel intensities for parameters that are specified on the pixel level.
   In cases wherein the diseased area is a map of local tissue characteristics determined on a per pixel basis, the average value will be calculated for each projection line and the average value will be projected onto the treatment surface. (E.G. perfusion imaging, deformation imaging, timing maps, stiffness maps, wall stress, expert input, simulation input)
3) Projection of characteristics that are specified by the radial projection lines.
   The radial projection lines may be used to assess tissue parameters of E.G. ventricular shape, wall thickness or, reachability by the devices. The crossing of the radial projection line with the treatment surface can be used to project aspects of the treatment surface (shape, reachability). When also the crossing of the radial projection line with other (organ or tissue) segmentations is taken into account, the local tissue thickness can be assessed and projected.
4) Projection of external organs
   When the distance to external organs is an important factor to determine the most eligible treatment location (e.g. in case of a nerve), the 3D location of the external organ of interest must be determined in patient coordinates. Hereafter the nearest distance from the external organ to each vertex of the treatment surface is projected on the treatment surface and used for treatment planning.

When the parameters of interest are projected onto the treatment surface, an interpolation algorithm is applied to homogenously distribute the parameters on the treatment surface. Next, the user applies the treatment planning algorithm by applying the threshold of the different parameters individually, ranging from 100% healthy to 100% diseased tissue, so that the area which is most eligible for the therapy is identified. This is referred to as the treatment area. For procedures where optimal visualization and catheter navigation is required, the user can be asked to select locations in the treatment area that are most easily accessible by the catheter. This may also be performed automatically. A treatment may be performed on the treatment surface or behind it, e.g. at an injection depth behind the treatment surface, the point of treatment being projected onto the treatment surface to form the treatment location at the treatment surface. To enhance the navigation accuracy, a single treatment location or a selection of treatment locations, may be stored in a treatment file so that no misinterpretation of different treatment locations can occur during the intervention.

E.g. depending on a type of treatment, the treatment location may be in the diseased area, at a border of the diseased area or outside the diseased area. For example, when applying stem cell injections in cardiac regeneration therapy, the stem cell injections are best performed in a mildly diseased area, which may e.g. be located at a border of the diseased area, as a regeneration process may provide a higher chance of success in such mildly diseased tissue. As another example, in cardiac regeneration therapy, a pacemaker electrode may be installed at tissue that is free from an infarct and that is responding to contraction stimuli, while being proximate to the diseased area.

When a treatment location has been selected, the treatment location and the treatment surface (or at least a part of the treatment surface surrounding the treatment location) are registered at the interventional medical imaging device. For example, the treatment file comprising data representative of the treatment location and the treatment surface may be registered at the interventional medical imaging device. By the registration, the interventional medical imaging device provides for scaling, orientation etc. of the treatment surface and treatment location to match a coordinate system of the interventional medical imaging device. Then, the interventional device is positioned so as to face the treatment surface at the treatment location, i.e. is positioned to directly interact with the treatment surface. For example, in the case of stem cell injections, an injection needle of the interventional device is positioned facing the selected treatment location at the treatment surface. The treatment surface may for example be formed by a surface of an organ, such as an outside surface of an organ, an inner surface of a blood vessel or an inner surface of a cardiac chamber (also referred to as endocardial surface). The treatment surface may be curved. A normal to a local tangent plane of the treatment surface of the tissue is determined, the local tangent plane facing the treatment location. The normal thus forms a direction perpendicular to the treatment surface at the treatment location. The treatment location may be on the treatment surface or in the tissue delimited by the treatment surface.

During the intervention, an interventional medical imaging device is used to provide medical imaging. The interventional medical imaging device may be of a same type as the diagnostic imaging device. Commonly, a different type of imaging is used. For example, the interventional medical imaging device may be an X-ray imaging device. Such a medical imaging device provides a 2 or 3 dimensional medical image. A position of the interventional device is however to be verified in 3 dimensions as well as possibly in angular orientations. The interventional medical imaging device is used to image at least a part of the interventional device (preferably a part of the interventional device that faces the treatment surface, i.e. a part of the interventional device neighbouring to the treatment surface) and the treatment location, so as to image a positioning of the interventional medical imaging device. According to an aspect of the invention, the imaging takes place from a first direction perpendicular to the normal (i.e. the normal that is perpendicular to the tangent plane at the treatment surface) to obtain first interventional image data.

Using the first interventional image data, a position of the interventional device is verified in two directions, namely in a direction of the normal and in a second direction perpendicular to the normal and perpendicular to the first direction. If required, the position of the interventional device may be corrected in the direction of the normal and/or in the second direction. Thus, verification and, if necessary, correction of the position of the interventional device may be performed at e.g. a low dose of radiation for the patient and/or for the person performing the intervention, as less iterations may be required, i.e. a lower number of interventional images may need to be taken.

An accurate positioning of the interventional device may provide an accurate position of application of the therapy. For example, when applying an electrode for cardiac resynchronisation therapy, an accurate positioning of the electrode may be crucial to a success of the therapy, as an accurate positioning of the electrode may provide an accurate stimulation of the tissue as desired. As another example, in case of stem cell injection therapy, the stem cells may be accurately injected at a desired position.

The act of intervention as such may be considered a method of treatment. The present invention however, although carried out in the context of a treatment, does not form a method of treatment. Instead, the invention relates to the problem how to verify a position of the interventional device. Verifying a position is an essentially technical process. The position of the interventional device is verified (determined) with reference to a treatment location at a treatment surface as derived from diagnostic medical imaging data, which diagnostic medical imaging data has been obtained by imaging by a diagnostic medical imaging device.

Furthermore, verification involves the measurement by the interventional imaging device. An orientation of the imaging is determined, so as to provide that the interventional image is taken from an angle that allows accurate verification of the position in respect of the treatment point, e.g. at a low error of perspective.

The verification may encompass displaying information that allows a person performing or supervising the intervention to verify the position of the interventional device and if necessary, adjust the position thereof. As another example, the verification may be performed by the data processing device and may result in a transmission of instructions to the interventional device for (semi) automatic positioning.

In an embodiment, -the method further comprises imaging, by the interventional medical imaging device, the treatment location and at least the neighbouring part of the interventional device from a third direction having a component in the first direction to obtain a second interventional image data, and enhancing, using the second interventional image data, a position of the interventional device in the first direction. Thus, a second image from another angle is taken, the other angle providing an image from the third direction. The third direction has a component in the first direction to enable to verify, using the second interventional image data, a position of the interventional device in the first direction. If required, the position of the interventional device may be corrected in the first direction. As a result, the position of the interventional device may be verified and/or adjusted from a low number of interventional images, which on the one hand may allow to reduce the number of interventional images taken during intervention (hence reduce a load of e.g. radiation to which the patient is subjected) and on the other hand increase a positioning accuracy, as the positioning is verified per dimension separately: A fine adjustment of the position of the interventional device in one direction may hence be prevented from disturbing a positioning accuracy of the interventional device in another direction.

When for example a C-arm X-ray device is used as an interventional imaging device the system is able to calculate the optimal angles of the C-arm to visualize the treatment location. Both the location of the selected vertex on the treatment surface, and the treatment surface in patient coordinates are used to calculate the angles of the C-arm for visualization of the treatment location in conjunction with the organ (e.g. the heart) so that accurate navigation of the interventional device may be ascertained. The calculation may be based on the normal to the treatment surface at the location of the selected vertex. The surface normal may be calculated from the mean inner-product of the faces which the vertex is connected to. Subsequently, the direction perpendicular to the resulting mean surface normal in the original image plane in patient coordinates is calculated. The direction of the last vector with respect to the operation table provides input to calculate the interventional device imaging angles that provide a perpendicular view at the treatment location. A second angle to display a slight off-angle view to confirm the position is calculated by an offset (15-90 degrees) from the perpendicular view. The angle of 15-90 degrees may be understood to be in any direction, e.g. forming a positive or a negative angle. A smaller angle towards 15 degrees will allow taking the second image with a short time between the images, while a larger angle may provide for a second image with a larger component in the first direction, hence may allow a more accurate positioning. The second angle may be obtained quickly and conveniently by rotating the interventional medical imaging device about a main axis of rotation. The main axis of rotation may be formed by an axis of rotation of a C-shaped arm having a radiation source on one end and an imaging sensor on the other end, about (i.e. around) an axis extending from head to feed of the patient. A balance between accuracy and speed may be found when the angle is between 30 and 60 degrees, more preferably around 45 degrees.

Alternatively, the interventional imaging device may be a so called bi-plane imaging device that takes images from dual directions, for example dual perpendicular directions. As another example, the interventional imaging device may be an interventional MRI system. The bi-plane imaging device may for example comprise two radiation sources and two detectors, a first radiation source and cooperating first detector forming an imaging direction at an angle relative to a second radiation source and cooperating second detector In such a bi-plane imaging device, the image from the first direction may be formed by a first image plane of the bi-plane imaging device, and the image in the third direction may be formed by a second image plane of the bi-plane imaging device, so that no additional rotation of the interventional imaging device may be required between the taking of the images from these two directions.

Thus, during the surgical or interventional procedure using e.g. standard interventional imaging equipment that is available during the surgery or intervention, treatment planning data obtained from diagnostic imaging and data processing (segmentation, etc.), may be applied in order to direct the interventional procedure by positioning the interventional device and positioning the interventional imaging device so as to take interventional images from angles as determined from the processed diagnostic data (i.e. the segmentation, treatment surface and treatment location). Hereby the surgeon or interventional physician may not need to rely solely on the superficial information of the organ obtained via eyesight or superficial measurements, but the information of the deeper tissue layers is also incorporated during the targeting of the therapy. With these techniques therapies may be targeted to the defined pathological locations, at a defined depth, and with a reproducible dose in all subjects and subjective operator depended decisions may be omitted.

The enhancing the positioning of the interventional device may be performed in various ways: for example, the enhancing may comprise a displaying of information that allows a person performing or supervising the intervention to verify the position of the interventional device and if necessary, adjust the position thereof. As another example, the enhancing may comprise transmission of instructions to the interventional device for (semi) automatic positioning.

Accordingly, in an embodiment, the enhancing, using the first interventional image data, the position of the interventional device in the direction of the normal and in the second direction perpendicular to the normal and perpendicular to the first direction, comprises fusing a display of the treatment point and the first interventional image data. The interventional image may be a two dimensional image. The fusing may allow to display the treatment location (and possibly also a view of the treatment surface) in combination with the interventional image, so that the position of the interventional device relative to the treatment location can reliably be distinguished.

In an embodiment, the enhancing, using the first interventional image data, the position of the interventional device in the direction of the normal and in the second direction perpendicular to the normal and perpendicular to the first direction, comprises sending instructions to the interventional device to adjust a position of the interventional device. Although the above describes the enhancing (by means of displaying a fused image and or sending of instructions) in the context of the first interventional image data, it will be understood that the same applies to the second interventional image data.

In an embodiment, a radiation load onto the body of the patient is optimized (e.g. minimized) using an absorption model, in that the method further comprises:
  providing an absorption model expressing a load by the interventional imaging device onto the body of the patient;
  calculating, using the absorption model, a load by the interventional imaging device onto the body of the patient as a function of a direction of imaging of the interventional imaging device; and
  adjusting at least one of the first direction and third direction based on the calculated load.

The higher an absorption of radiation (such as X-ray radiation) by the body of the patient, the higher an output power of the interventional medical imaging device will be set, hence the higher a radiation load on the body of the patient. The absorption may be calculated, for different directions of imaging, using the model, e.g. stepwise incrementing/decrementing the direction in the calculation. A direction at which absorption is low may be selected. The first and/or third direction may hence be adjusted based on the calculated load and the direction at which an optimum (e.g. low or lowest) absorption has been found according to the model, prior to imaging from the respective direction by the interventional imaging device. Hence, the imaging by the interventional imaging device may be performed at a reduced load to the patient.

In an embodiment according to any aspect of the invention, the method comprises:
  selecting, in the diagnostic medical imaging data, a cross sectional plane defined by the normal to the local tangent plane of the treatment surface and the second direction; and
  displaying a resulting diagnostic medical image of the cross sectional plane with a display of the interventional medical imaging data.

When angle calculation has been performed and interventional medical imaging device angles have been calculated, this can serve as an input to create a cross-sectional view of the treatment dataset and/or the diagnostic imaging dataset from the same viewpoint as the interventional image. To provide this a 3D reconstruction may be created of the treatment file, from which a cross-sectional plane may be selected so that the surface normal of the local tangent plane to the treatment surface at the treatment location lies in the image plane. The resulting treatment data and/or diagnostic imaging data) may be represented from the viewpoint of the C-arm (the interventional imaging device) and may be displayed on a second screen during the intervention to support the user by visualizing the diagnostic medical imaging (MRI, CT, Ultrasound) data with its superior soft tissue contrast from the perspective of the C-arm. Alternatively, the images may be fused into a single image to display the treatment data and/or diagnostic medical imaging data, e.g. the treatment site and/or the segmentation in the interventional image.

In an embodiment according to any aspect of the invention, the method according to the invention comprises:
  recognizing, in the diagnostic medical imaging data, an organ other than the tissue at which the treatment surface is defined,
  calculating, for each point in the segmented medical image data, a distance from the organ to the point in the segmented medical image data, and
  wherein the defining the treatment location comprises taking account of the calculated distance from the organ to the point in the segmented medical image data.

Furthermore, so called no-go area's may be defined, being area's on the treatment surface in which no treatment is to be performed, i.e. where no treatment locations are desired, for any reason, e.g. because of a severity of the disease in that area, because of a presence of a risk factor, or for any other reason.

When the distance to external organs (e.g. in case of a nerve) is a factor to determine the most eligible treatment location, a 3D location of the external organ of interest may be determined in patient coordinates. Hereafter a nearest distance from the external organ to each vertex of the treatment surface may be projected on the treatment surface and used for treatment planning. For example, taking account of the calculated distance may comprise maintaining a predetermined minimum distance between the organ and the treatment location so as to keep a safe distance.

Likewise, a "no-go" area may be defined in e.g. the segmented medical imaging data or on the treatment surface, so as to defined an area where no treatment is desired. Thus, safety may be increased as an area's where no treatment is desired, may e.g. be identified by a user.

The present embodiment may, but not necessarily needs to be combined with the method according to the first aspect of the invention. The present embodiment may also be applied as such. Accordingly, according to a second aspect of the invention, there is provided:

A method of defining a treatment location in an image of tissue of a patient, the method comprising:
  providing by a diagnostic medical imaging device, medical image data representing a diagnostic medical image of the tissue of the patient;
  segmenting, using an image segmentation criterion, in the diagnostic medical image data a diseased area image data representing a diseased area of the tissue;
  defining, in the segmented image data of the diagnostic medical image data, a treatment location;

wherein the method further comprises:
recognizing, in the diagnostic medical imaging data, an organ other than the tissue at which the treatment surface is defined,
calculating, for each point in the segmented medical image data, a distance from the organ to the point in the segmented medical image data and
wherein the defining the treatment location comprises taking account of the calculated distance from the organ to the point in the segmented medical image data.

In an embodiment according to any aspect of the invention, the method further comprises copying the treatment location from the diagnostic medical image data to the interventional medical image data, and highlighting, in the interventional medical image data as obtained by the interventional imaging device, the copied treatment location.

The treatment location(s) may be saved in a treatment file e.g. in a Digital Imaging and Communications in Medicine (DICOM) format or a Neuroimaging Informatics Technology Initiative (NIfTI) format or other medical imaging format, that may be compatible with the interventional imaging system. Hereafter referred to as the treatment file. DICOM files typically contain a header section with macro information about the patient and study. Besides the macro information the DICOM files contain a section with the image information (typically with 16 bits/pixel).

The created treatment file has the same header information as the image file used for the segmentation and the treatment planning algorithm. To uniquely identify the treatment file, a tag may be added in the header stating that it is a file created for treatment planning purposes. Moreover the treatment file of a specific treatment location may be stored in a folder with a name that contains a reference to the treatment location.

The position of a treatment location may be derived from the treatment area determined by the treatment planning algorithm and the user or automatic selection of a location that is most appropriate for treatment. The aforementioned steps lead to a location with X, Y, Z values that specify a vertex on the 3D treatment surface. The vertex location is transferred to the 2D image plane or the 3D image dataset, and in the image plane or the dataset the location of the nearest pixel to the vertex location is selected. To change the pixel data in the medical image, the concerning image is opened by a binary read command. Of the information available first the location of the start bit of the image needs to be specified, e.g. as a hexadecimal value in a 16 bit image. When the start bit is determined, the data is read from the start bit to the end bit so that 16 bits represent a single pixel. Subsequently the location of the pixel that needs to be modified is selected based on its index number. The index number is calculated from the position in the 2D image or 3D image dataset by concatenating all columns. User input may be required to specify the amount and/or the brightness of the pixels that are modified to visualize the treatment location in the treatment file. The treatment file is stored in the medical imaging format from which it is created with an added tag that indicates the stored image to be a treatment file.

The present embodiment may, but not necessarily needs to be combined with the method according to the first aspect, and/or second aspect of the invention. The present embodiment may also be applied as such. Accordingly, according to a third aspect of the invention, there is provided:

A method of identifying a treatment location in interventional medical image data provided by an interventional medical imaging device, the method comprising:

providing, by a diagnostic medical imaging device, medical image data representing a diagnostic medical image of the tissue of the patient;
segmenting, using an image segmentation criterion, in the diagnostic medical image data a diseased area image data representing a diseased area of the tissue;
defining, in the segmented image data of the diagnostic medical image data, a treatment location;
copying the treatment location from the diagnostic medical image data to the interventional medical image data, e.g. at its respective 3D location, and highlighting, in the interventional medical image data as obtained by the interventional imaging device, the copied treatment location.

The copying the treatment location from the diagnostic medical image data to the interventional medical image data may be performed in many ways. For example, a treatment file is created from the diagnostic medical imaging file and the treatment location is highlighted in the treatment file. Then, the treatment file is registered at the interventional medical imaging device, i.e. with the interventional medical imaging data. In this way, the ability of imaging systems to register a previously obtained image, e.g. for simultaneous display, is made use of, so as to enable to combine the diagnostic and interventional image data using existing software routines. Many alternatives are possible. For example, the coordinates of the treatment location may be transferred from the treatment file to the interventional medical imaging data.

In an embodiment according to any aspect of the invention, the method comprises:
providing a geometric outline model of the interventional device;
determining in the diagnostic medical image data, an available space facing the treatment surface, —modelling, at the treatment location in the diagnostic medical image data, the geometric outline model of the interventional device in the available space, and—confirming the treatment location if the geometric outline model of the interventional device fits in the available space at the treatment location. Furthermore, based on the determined available space, the optimal interventional device for a specific treatment location may be selected from a plurality of available (and e.g. differently sized) interventional devices.

Thus, before bringing the interventional device to the treatment location, it is calculated if the interventional device would fit. For example, in a cardiac chamber, some area's may be better accessible than others. For each treatment location as identified above, the model of the interventional device may be placed in the available space, and if the model of the interventional device fits in the available space when facing a respective one of the treatment locations, the respective treatment location may be confirmed. Otherwise, either another treatment location may be selected or a smaller or larger interventional device (such as a smaller probe or stimulation wire) may be applied instead.

In an embodiment, the method comprises: segmenting, in the diagnostic medical imaging data, a cavity, (E.G. a main blood vessel or an atrium), segmenting, in the diagnostic medical imaging data, a blood vessel which directly connects to the cavity; defining the treatment surface as an overlap of a cross sectional surface of the segmented blood vessel and a surface of the cavity. The cavity may for example be the right atrium, whereby the blood vessel may for example be the coronary sinus vene. In cardiology, it may be desired to guide an interventional device into a blood vessel which blood vessel leads into an atrium of the heart, such as the coronary sinus vene. As another example, the cavity may be the aorta and the blood vessel may be the coronair artery. A segmentation is performed on the diagnostic medical imaging data to distinguish the cavity (e.g. the atrium) and to distinguish the blood vessel (e.g. the coronary vessel). Then, from the segmentations, a surface of interest is derived as an overlap of the cross sectional surface of the segmented blood vessel (e.g. coronary vessel) and the surface of the cavity (e.g. the atrium). After the interventional device has been brought into the cavity (e.g. an atrium of the heart), an imaging is taken to establish a position of the interventional device in respect of the opening where the blood vessel (e.g. the coronary vessel) discharges into the artery. This surface of interest may be highlighted in the interventional medical imaging data, so as to provide guidance to a person regarding a present position of the interventional device. Furthermore, in order to efficiently acquire the interventional images e.g. at a low radiation load to the patient, the surface of interest may, likewise to the treatment surface, be used as a reference to determine the first direction and optionally the third direction of imaging as explained above, in order to enable obtaining the interventional images from the first and optionally the third angle.

The invention may be implemented in a form of a data processing device, such as a computer, that receives diagnostic medical image data from the diagnostic medical imaging device, and provides instructions for the intervention. The instructions may be angular data providing an imaging angle for the interventional medical imaging device and position data providing a desired position of the interventional device so as to face the treatment location.

Accordingly, according to an aspect of the invention, a data processing device is provided for connection to a diagnostic medical imaging device and a an interventional medical imaging device, the data processing device being provided with program instructions for making the data processing device perform the steps of:
  receiving, from the diagnostic medical imaging device, diagnostic medical image data representing a diagnostic medical image of the tissue of a patient;
  segmenting, using an image segmentation criterion, in the diagnostic medical image data a diseased area image data representing a diseased area of the tissue;
  identifying, in the segmented diagnostic medical image data, a treatment surface of the tissue;
  projecting the treatment location diseased area, represented by the diseased area image data, onto the treatment surface;
  defining a treatment location on the treatment surface;
  registering data representative of the treatment surface and the treatment location at an interventional imaging device;
  positioning the interventional device to face the treatment surface;
  determining a first direction perpendicular to a normal to a local tangent plane of the treatment surface of the tissue, the local tangent plane being located at the treatment location on the treatment surface;
  providing instructions to the interventional medical imaging device for imaging, by the interventional medical imaging device, at least a part of the interventional device and the treatment location to obtain first interventional image data from the first direction and
  providing instructions for enhancing, using the first interventional image data, a position of the interventional device in a direction of the normal and in a second direction perpendicular to the normal and perpendicular to the first direction.

According to a further aspect of the invention, there is provided a software program product comprising program instructions configured to, when loaded into a data processing device, make the data processing device perform the steps as described above. With the data processing device and the software program product, the same or similar effects may be achieved as described with reference to the method according to the invention. Also, the same or similar embodiments as described with reference to the method according to the invention may apply.

The invention further encompasses a system comprising a diagnostic medical imaging device, an interventional medical imaging device, and a data processing device according to an aspect of the invention, the data processing device being connected with the diagnostic medical imaging device and the interventional medical imaging device.

The invention further encompasses a use of a data processing device according to an aspect of the invention, the data processing device being connected with a diagnostic medical imaging device and an interventional medical imaging device.

Further advantages, features and effects of the invention will follow from the appended drawing and corresponding description, disclosing a non-limiting embodiment, wherein.

Figure 1:
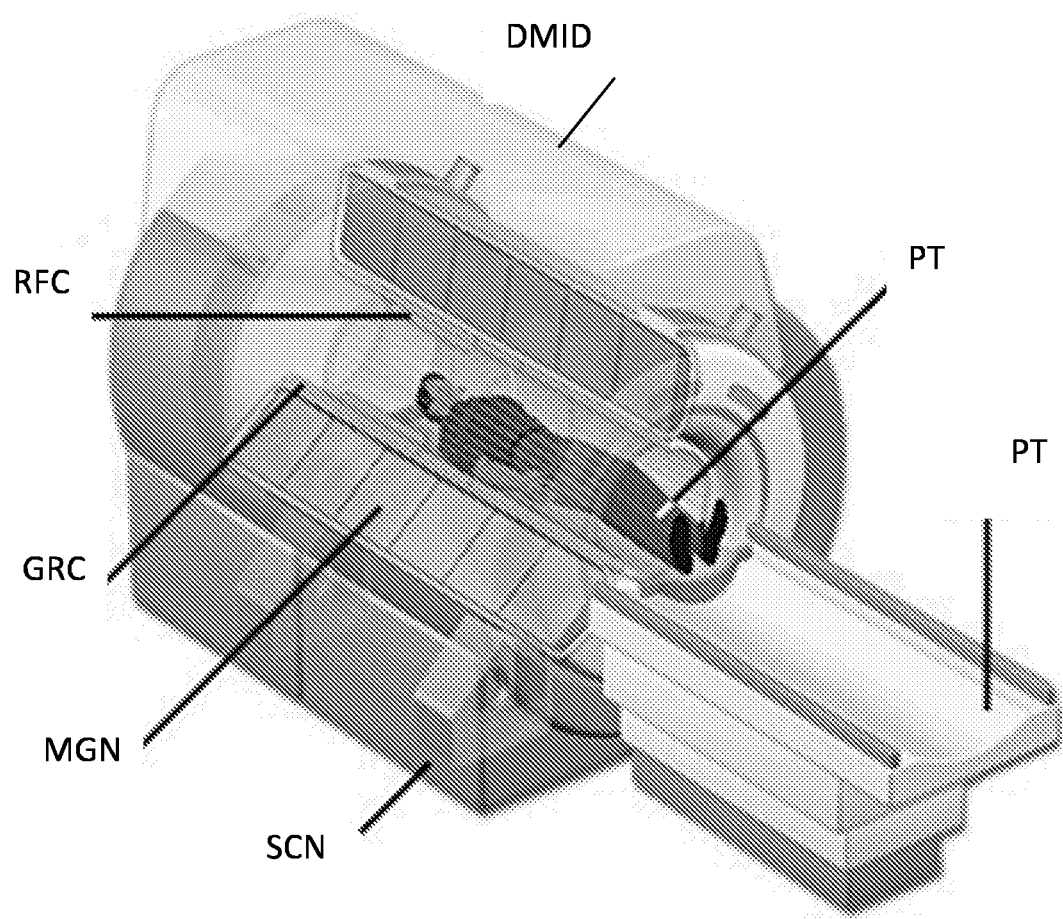
FIG. 1 depicts a diagnostic medical imaging device.
Figure 2A:
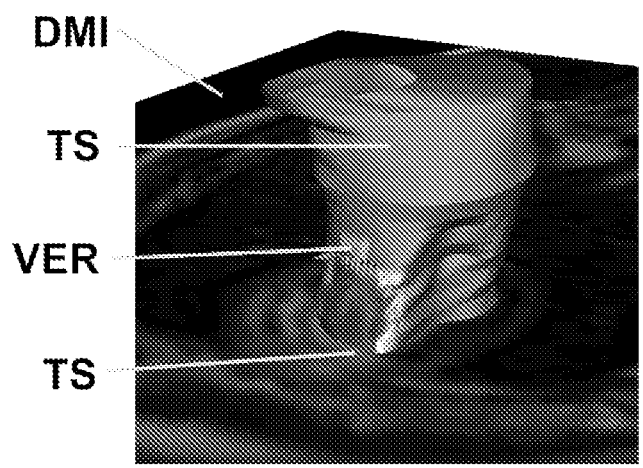
FIGS. 2A and 2B depict an example of a visualisation of diagnostic medical image data showing an endocardial chamber.
Figure 2B:
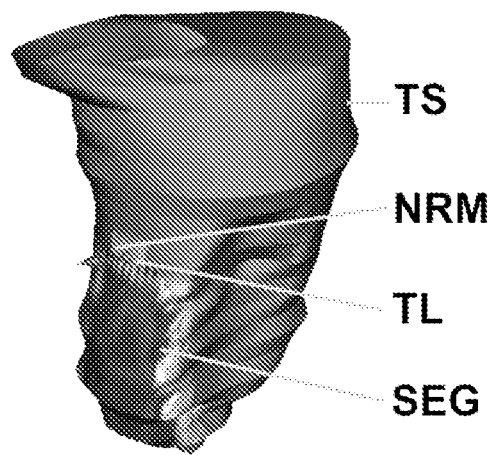
Figure 3A:
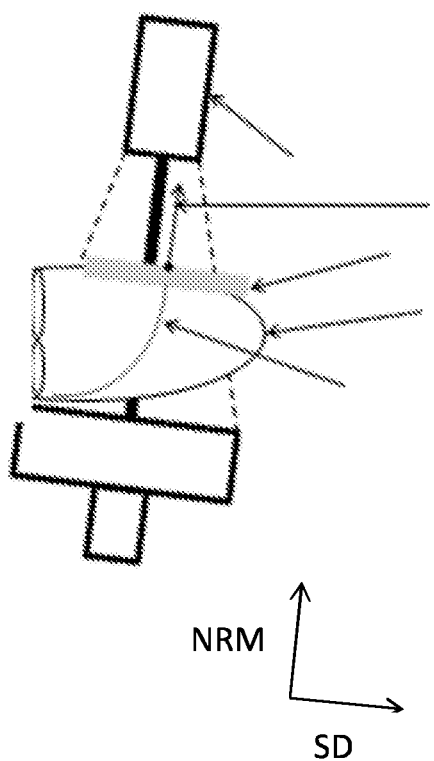
FIG. 3A and 3B depict view of a highly schematic representation of an interventional medical imaging device.
Figure 3B:
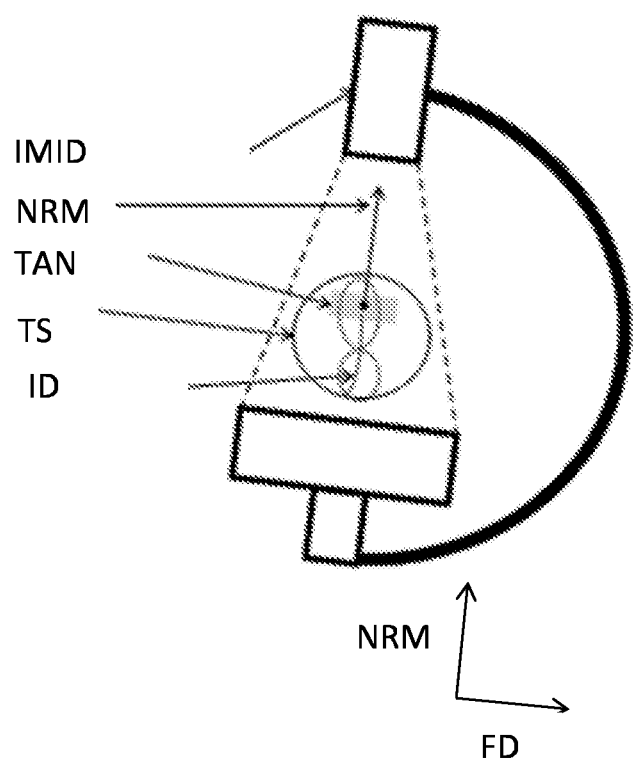
Figure 4:
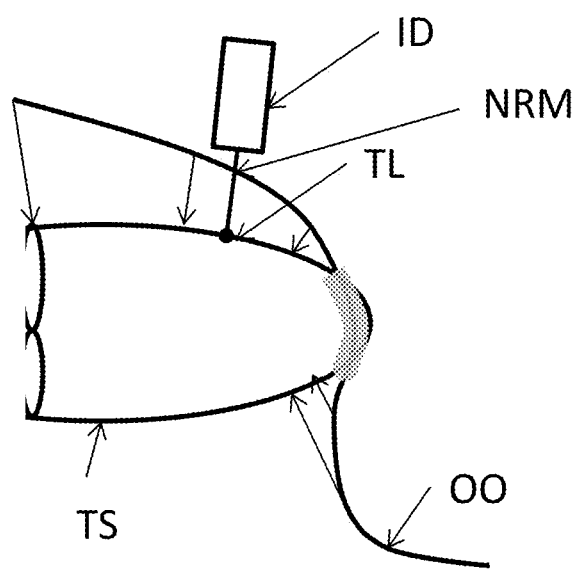
FIG. 4 depicts a highly schematic representation of a visualisation of interventional medical image data.

FIG. 1 depicts an example of a diagnostic medical imaging device DMID, in the present example an MRI (magnetic resonance imaging) device. A patient PT, or part of a body of a patient, lying on a patient table PT, is imaged, resulting in medical imaging data from the diagnostic medical imaging device, hereinafter referred to as diagnostic medical image data DMI. The MRI device comprises a radio frequency coil RFC, gradient coils GRC, a magnet MG. and a scanner SCN. The diagnostic medical image data may be 2 dimensional, 3 dimensional or 3 dimensional plus time (referred to as 4 dimensional). FIG. 2A depicts an example of a (visualized) diagnostic medical image data. The diagnostic medical imaging data may be any data format. An organ or part thereof is identified in the diagnostic medical imaging data. FIG. 2A depicts an example where a cardiac chamber is identified. A surface mesh is fitted to a surface of the organ, as depicted in FIG. 2A, providing a treatment surface TS. In the present example, an endocardial surface of the heart. is depicted. The diagnostic medical imaging data relating to the organ is segmented, using any of the described segmentation techniques, so as to identify an area that is potentially diseased. FIG. 2B depicts a visualized segmented diagnostic medical image data comprises a segmented part SEG of the tissue. A treatment location TL is selected in the segmented diagnostic medical imaging data, for example in a zone of the segmented part of the tissue having a predetermined disease severity. The treatment surface TS is identified, in the present example as an inner surface of the organ. In other examples, the treatment surface may be an outer surface, for example an epicardial surface. The treatment location TL is projected on the treatment surface. A surface normal NRM is determined by selecting a vertex VER on the treatment surface that is closest to a location on the treatment surface where the treatment location is projected onto the treatment surface. The diagnostic medial image data is registered at an interventional medical imaging system so as to provide that the diagnostic medial image data may be registered and viewed with interventional medical image data as provided during an intervention. The registering may comprise scaling and matching coordinate systems so as to fit the diagnostic image onto an interventional coordinate system applied during the intervention. Scaling of the image is provided so as to display the diagnostic image with the interventional image and to match diagnostic medical imaging and interventional medical imaging coordinate systems for corresponding image orientation. FIG. 3A and 3B provide a schematic representation of the treatment surface TS (being the endocardial chamber) as depicted in FIG. 2B, wherein the organ has been tilted 90 degrees (the person being in a horizontal position). The treatment location TL as depicted in FIG. 2B hence corresponds to the treatment location at the origin of the surface normal NRM as depicted in FIG. 3A and 3B. In the diagnostic medical image, a tangent plane TAN of the treatment surface is determined (as schematically depicted in FIG. 3A) at the projected location of the treatment location. The surface normal NRM, i.e. a direction perpendicular (normal) to the tangent plane, is depicted. FIG. 3A and 3B depict an interventional medical imaging device IMID, in the present example an X ray device. As the diagnostic medical imaging data, e.g. the treatment location, the treatment location as projected onto the treatment surface and the surface normal, are registered at the interventional medical imaging device, the diagnostic medical imaging data, including e.g. the treatment location, may be depicted in the interventional medical images. A catheter or other interventional device ID may be inserted in the body so as to reach the organ. In the present example a catheter reaches the cardiac chamber via a blood vessel. In order to verify a position of the catheter, an image is taken by the interventional medical imaging device. A direction for taking the image is calculated as being perpendicular to the normal NRM. The interventional imaging device is rotated according to that direction. Thereto, angular data providing information about a desired angle of imaging may be provided to the interventional medical imaging device. Then, the image is taken from a first direction perpendicular to the normal. A resulting image is schematically depicted in FIG. 4. The image depicts an image plane in a direction of the normal and a second direction SD perpendicular to the normal and to the first direction FD. A position of the interventional device ID in the direction of the normal and the second direction may be verified and if needed, adjusted, after which the taking of the interventional image may be repeated to verify the adjusted position if desired.

In order to adjust the position of the interventional device in a direction perpendicular to the plane of the drawing, the interventional medical imaging device may be displaced, e.g. rotated, so as to image from a third direction. The third direction may be achieved by a rotation of the interventional imaging device about an axis of rotation thereof, e.g. a main axis of rotation as defined by the C shaped holder of the interventional medical imaging device. The rotation may be at or near 90 degrees so as to angularly distinguish this image from the previous one, or less (e.g. 15-90 degrees, for example 45 degrees) so as to enable to take this image within a short time after the image in accordance with the plane of FIG. 4, as less rotation of the interventional device will be required. A balance between accuracy and speed may be found when the angle is between 30 and 60 degrees, more preferably around 45 degrees.

Alternatively, the interventional medical imaging device may comprise dual interventional imaging devices, e.g. at 90 degrees in respect of each other, thus providing, together with the imaging in the plane in accordance with FIG. 4, a second interventional medical image at an angle of 90 degrees thereto.

The treatment surface may be defined by a plurality of vertices and the normal to the local tangent plane may be determined by selecting a vertex on the treatment surface which is nearest to the treatment location. The normal may be determined from that vertex by equating the normal to the vertex. Alternatively, plural neighbouring vertices may be taken, and the normal set to an average thereof.

The higher an absorption/attenuation of radiation (such as X-ray radiation) by the body of the patient, the higher an output power of the interventional medical imaging device will be set, hence the higher a radiation load on the body of the patient. The absorption may be calculated, for different directions of imaging, using an absorption model, e.g. stepwise or continuously incrementing/decrementing the direction in the calculation. A direction resp. directions at which absorption is resp. are low may be selected. The first and/or third direction may hence be adjusted (i.e. amended) based on the calculated load and the direction at which an optimum (e.g. low or lowest) absorption has been found according to the model, prior to imaging from the respective direction by the interventional imaging device. Hence, the imaging by the interventional imaging device may be performed at a reduced load to the patient.

When displaying the interventional image, a cross sectional view of the diagnostic medical image data along a plane coinciding with the image plane of the interventional image may be taken and displayed, so as to provide that diagnostic image data, incl. e.g. segmentation, treatment location and treatment surface are displayed from a same angle, providing additional information for positioning and intervention. The plane in the (3D) diagnostic medical imaging data to be displayed may be formed by the normal to the tangent plane of the treatment surface, determined as described above, and the second direction. In a two dimensional view, estimating a distance to other organs may be difficult, as dimensions in 3D may be misinterpreted from 2D images. Hence, when determining the treatment location, a location may be selected that would be too close to another organ OO. In an embodiment, in order to determine the treatment location(s), other organs may be recognized (automatically or manually) in the diagnostic medical imaging data, and a (3D) distance to such other organ OO may be calculated for a plurality of locations (points) on the treatment surface. The treatment location may take account of the calculated distance, e.g. by keeping a predetermined minimum distance between the treatment location and the other organ OO. As a result, risks and/or possible adverse effects as a result of applying a treatment near that other organ, may be reduced, e.g. reducing a risk of damage to the other organ OO.

Furthermore, in order to identify the treatment location (as defined in the diagnostic medical imaging data) during the interventional procedure, after mapping (e.g. scaling) the diagnostic medical imaging data onto the interventional medical imaging data, the treatment location may be copied to the interventional medical imaging data in that at least one pixel in the interventional imaging data at a position corresponding to the treatment location as defined in the diagnostic medical imaging data, is highlighted by setting an intensity thereof to a high level, e.g. a level higher than a normal imaging intensity range of the interventional image. The copying to the interventional medical imaging data may for example be performed by registering a treatment file comprising the (e.g. highlighted) treatment location, at the interventional medical imaging device, and displaying this information at the interventional medical imaging device.

In order to prevent damaging neighbouring tissue by the catheter, or discovering during the intervention that the catheter does not fit in an available space at the treatment location, an available space near the treatment location may be identified in e.g. the (3D) diagnostic medical imaging data, a 3D model of the interventional device may be fitted into the available space near the treatment location, so as to estimate if the interventional device would fit. These calculations may be performed e.g. before bringing the interventional device into the patient's body, so as to estimate if the selected device would fit or not, and if not, to either select another therapy location or another, e.g. a smaller, interventional device.

An example of a non-limiting embodiment incorporating various aspects of the invention is provided below.

1. Providing a diagnostic medical image. A medical image is taken by a diagnostic medical imaging device. The diagnostic medical imaging device may be a CT, MRI, SPECT, PET, Ultrasound or any other medical imaging device. The medical image may be a two dimensional image, a sequence of 2 dimensional images, each spaced apart in a third dimension perpendicular to the 2 dimensions of the images, so as to provide 3 dimensional information, or a 3 dimensional image. Also, a 2 or 3 dimensional image may have been taken as described above, at different time instances, whereby the images are combined into a 4 dimensional image. The image may be an image of any suitable tissue of the patient, e.g. any suitable organ, such as a heart, lung, liver, etc. The diagnostic medical image may be composed from plural imaging devices, e.g. a combination of MRI and an echoscopic image, whereby for example Doppler information is obtained from the echoscopic image, etc.

2. Image segmentation. An organ segmentation is created of the organ of interest. The result of the organ segmentation process is a two or three dimensional spatial object representing at least the treatment surface of the organ of interest. The anatomy, pathology or other tissue or organ characteristic that is used for treatment planning is processed using a specific technique for each parameter. Techniques used are the automatic or manual segmentation of the organ and specific areas within the organ, or result from the analysis of specific characteristics within the segmented organ or the unsegmented medical image. The resulting disease presence or severity is reconstructed into a two or three dimensional spatial object. Both the treatment surface and the diseased area are now positioned with respect to each other and the disease presence or severity is projected onto the treatment surface using a radial projection technique.

3. Mesh creation. A 3D surface mesh is created of the surface of the organ or tissue whereto the therapy will be provided. A mesh of the internal side of the organ is used for internal/endocardial therapies, and a mesh of the external side of the organ is used for external/ epicardial therapies. The 3D surface mesh is created by connecting the points of the 2D image segmentations so that the nearest points in different consecutive image slices are connected. To ensure a sufficient mesh resolution extra vertices may be interpolated between two slices. To prevent obliqueness of the mesh faces between consecutive slices a correction algorithm may be applied to minimize the distance between connected vertices of two consecutive slices.

4. Quantification
   a. The organ segmentation and the medical image are subjected to an algorithm to assess the local tissue characteristics based on E.G. image intensity, timing values or other tissue specific parameters. Local tissue characteristics are determined by an algorithm which has as an input the image segmentation and the medical image. The algorithm determines the local tissue characteristics and returns the values for each pixel or combination of pixels in the segmented tissue.
   b. The 3D organ segmentation is used as an input to derive local organ (geometry) characteristics. The reachability can either be used for treatment planning by manual selection of treatment locations, or can be calculated by an algorithm. For each device the locations in the organ that are easy or difficult to access can be specified. The reachability is based on the entrance location of the organ, the organ geometry and the properties of the interventional device to be used. In contrast treatment planning can be used to specify the interventional device properties to optimally access the treatment point.
   c. The 3D organ segmentation and the medical image are subjected to an algorithm to allow external aspects to be incorporated during the treatment. Therefore a separate segmentation is done of the organ(s) that are sensitive for interference with the therapy. A value representing the likelihood or severity of the interference is used as a parameter during treatment planning. Alternatively an expert system is used to incorporate predefined knowledge about the optimal therapy location. Therefor one or a combination of different tissue, organ or patient characteristics are matched to a database which contains the therapeutic results of patients that have been treated with the same therapy earlier. Moreover a simulation model might be used to predict the outcomes of the therapy in a patient or population specific fashion and thereby serve as an input to select the optimal treatment location. A value is assigned to all the vertices of the 3D surface and used for treatment planning.

5. Projection. The datasets that result from the quantification step are used as an input for a projection algorithm to project the local tissue or organ characteristics on the surface mesh.
   a. Tissue characteristics of which a gradient can be expected in the tissue (e.g. fibrosis, perfusion, deformation), or a parameter that is derived from these characteristics, will be projected on the surface mesh using radial projection. The radial projection divides the tissue in equal segments so that each vertex of the surface mesh is part of one segment that contains both the inner and outer segmentation. For spatially spaced parameters in each segment (E.G. timing, intensity) the value projected on the surface mesh vertex is equal to the average value of all the spatially spaced parameters in the segment. For parameters with a single value in each segment that is related to the segment (E.G. wall thickness, infarct transmurality), a line is drawn through each point of the surface mesh and the relative value of the parameter with respect to the segment is calculated and projected on the surface mesh vertex.

b. Organ characteristics of which a local difference can be expected (curvature, wall stress, device reachability) are derived from the surface mesh and therefore inherently the surface mesh has a value on all vertices.

c. External inputs that are derived from one or a combination of the interfering organs, expert system or simulation model are projected on the surface mesh and therefore inherently the surface mesh has a value on all vertices.

The radial projection algorithm divides the organ (in this case e.g. the left ventricle) into a finite number of equally spaced segments that are oriented perpendicular to the treatment surface at the intersection point of the treatment surface and the projection line. The intersection points are located at the vertices of the treatment surface mesh. To project the parameter of interest on the treatment surface three types of projections can occur:

1) Projection of the presence or absence of the disease.
   A binary 1 is projected onto the treatment surface when the diseased area is crossed by a projection line. (E.G. fibrosis imaging).
2) Projection of pixel intensities for parameters that are specified on the pixel level.
   In cases where the diseased area is a map of local tissue characteristics divided per pixel basis, the average value will be calculated for each projection line and the average value will be projected onto the treatment surface. (E.G. perfusion imaging, deformation imaging, timing maps, stiffness maps, wall stress, expert input, simulation input).
3) Projection of characteristics that are specified by the radial projection lines.
   The radial projection lines may be used to quantify tissue parameters of E.G. ventricular shape, wall thickness or reachability by the devices. The crossing of the radial projection line with the treatment surface can be used to project aspects of the treatment surface (shape, reachability). When also the crossing of the radial projection line with other (organ or tissue) segmentations is taken into account, the local tissue thickness can be projected.
4) Projection of external organs
   When the interference of or on external organs is an important factor to determine the most eligible treatment location, the 3D location of the external organ of interest must be determined in patient coordinates by means of (semi-) automatic segmentation. Hereafter the nearest distance from the external organ to each vertex of the treatment surface is projected on the treatment surface and used for treatment planning.

6. Interpolation. When data is used that does not assign a value to all the vertices of the surface mesh, a 3D spatial linear interpolation algorithm is used to interpolate the projected values to the interpolated mesh vertices after projection of the available data on the 3D surface mesh. Alternatively data with a low spatial resolution is projected so that a clinically relevant projection of data over the surface mesh is obtained. When the parameters of interest are projected onto the treatment surface, an interpolation algorithm is applied to homogenously distribute the parameters on the treatment surface. Next the user applies the treatment planning algorithm by applying the threshold of the different parameters individually, ranging from 100% healthy to 100% diseased tissue, so that the area which is most eligible for the therapy remains. This is referred to as the treatment area. For procedures where optimal visualization and catheter navigation is required the user can be asked to select locations in the treatment area that are most easily accessible by the catheter. To enhance the targeting accuracy a single treatment location may be stored in each treatment file so that no misinterpretation of different treatment locations can occur during the intervention.

Contour/isoline. The interpolated values on the mesh are subjected to a contour/isoline algorithm to allow the physician to select the region based on a range of values that are most appropriate for the therapy. The threshold values can also be fixed. The contour/isoline algorithm connects all the mesh vertices with equal values and applies a filtering step in order to obtain a continuous and smooth isoline. The upper and lower bound of the treatment zone are combined into a 3D region on the surface mesh that is appropriate for the therapy and in a region where therapy should not be performed for safety or efficacy reasons.

8. Multiple parameters. A treatment plan can be based on multiple input parameters.
   a. By using multiple parameters for the treatment area calculation the resulting 3D region is based on different parameters that are aligned and result in a single treatment area. To allow a different contribution of different parameters to the treatment area calculation, a weighing factor can be determined and used for each parameter.
   b. When multiple parameters originate from different imaging techniques that are acquired at multiple time points, the different imaging datasets must be registered before treatment planning is performed.

9. Treatment points. In the treatment areas on the 3D surface mesh, the physician can manually determine specific treatment locations. Treatment locations are locations in the treatment area that are assessed by the physician to be most appropriate for the therapy.

10. Treatment file. The treatment file contains all the information that is necessary for an optimal intervention.
    a. The treatment points that are located on the surface mesh are transferred to the corresponding 3D location in the treatment dataset which is used for the treatment planning. On the location of the treatment point the pixel value, or the pixel values of a block of pixels of the treatment dataset is/are intensified to the maximum value that is permitted by the applicable standard (such as the DICOM or Nifti standard. The metadata of the treatment dataset is kept constant. The name of the treatment file is adapted so that the name of the treatment point is referenced in the filename.
    b. To promote optimal 3D navigation the 3D surface mesh can also be transferred to the corresponding 3D location in the treatment image dataset used for the treatment planning. Either this is done by intensifying the value of a predefined number of intermittent pixels at the location of the organ surface, or by visualization of a 3D wire mesh in the images.

c. In cases where the diagnostic image contains all the necessary information about the optimal therapy location, E.G. for surgical procedures, steps 1-7 may be skipped and the treatment location may be directly determined by the physician in the medical image. On the location of the treatment point the pixel value, or the pixel values of a block of pixels of the treatment dataset is/are intensified to the maximum value that is permitted by the used medical imaging standard. The metadata of the medical imaging dataset is kept constant. The name of the treatment file is adapted so that the name of the treatment point is referenced in the filename.

11. Interventional imaging device settings. Based on both the surface mesh and the treatment point, the optimal position and orientation of the interventional imaging device are calculated so that the physician can optimally visualize the therapeutic device in combination with the treatment location. This enables standardization of the procedure and shortens procedure time.

12. Interventional imaging. The treatment file is loaded into the interventional imaging device (fluoroscopy, MRI or Ultrasound).
    a. The registration of the treatment file on the live interventional imaging device is done by using the suite that is available for interventional imaging devices. Treatment images are registered with the interventional imaging device based on anatomical or fiducial landmarks that are visible in both the interventional and diagnostic imaging datasets.
    b. The registration of the treatment file and the interventional imaging device is done by dedicated software. The live interventional images and the treatment images are registered based on a combination of the anatomical or fiducial landmarks that are visible in both the interventional and diagnostic imaging datasets, and on the motion information that is derived from motion available in diagnostic images and live images from the interventional device.

13. Interventional guidance. Different guiding technologies can be used during the intervention.
    a. Therapy guidance to the optimal location can be done using manually steered catheters and the interventional imaging device for visualization of both the live image and the treatment plan.
    b. When the interventional imaging device uses ionizing radiation for imaging it is often attempted to minimize the amount of radiation. To minimize the radiation during the interventional procedure the interventional device can be visualized using a magnetic tracking technology. Therefore the interventional device is equipped with a miniaturized coil and a magnetic field can be generated in the patient's body by an external device. In this way the catheter can be visualized in concordance with the treatment plan without using ionizing radiation.

Another option is the use of a remote or robotically steered device to steer the interventional device to the optimal location. Either or not the device can be visualized using ionizing radiation or be equipped with a magnetic tracker to visualize its location.

The determining of the first and third directions for imaging, as described above, and the highlighting, in the interventional medial image, of an area of interest, may not only be performed on a physical treatment surface. As an alternative, the treatment surface may extend over an opening, such as an exit of an artery or vene, e.g. an exit of an artery or vene respectively from or in a cavity like a blood vessel (such as the aorta) or an atrium. A segmentation may be performed on the diagnostic medical imaging data to identify a cavity and a blood vessel which directly connects to the cavity; and the treatment surface may be defined as an overlap of a cross sectional surface of the segmented blood vessel and a surface of the cavity. The cavity may for example be the right atrium, whereby the blood vessel may for example be the coronary sinus vene. After the interventional device has been brought into an atrium of the heart, an imaging is taken to establish a position of the interventional device in respect of the opening where the coronary sinus vene discharges into the artery. This surface of interest may be highlighted in the interventional medical imaging data, so as to provide guidance to a person regarding a present position of the interventional device. Furthermore, in order to efficiently acquire the interventional images e.g. at a low radiation load to the patient, the surface of interest may, likewise to the treatment surface, be used as a reference to determine the first direction and optionally the third direction of imaging as explained above, in order to enable obtaining the interventional images from the first and optionally the third angle.

The invention may also be defined by the following numbered clauses with form part of the description:

1. A method of positioning an interventional device at a treatment location in a tissue of a patient, the method comprising:
    receiving from a diagnostic medical imaging device, diagnostic medical image data representing a diagnostic medical image of the tissue of the patient;
    segmenting, using an image segmentation criterion, in the diagnostic medical image data a diseased area image data representing a diseased area of the tissue;
    defining, in the segmented diagnostic medical image data, a treatment surface of the tissue;
    projecting the diseased area, represented by the diseased area image data, onto the treatment surface;
    defining a treatment location on the treatment surface, the treatment location being in, out or at a boundary of the diseased area projected onto the treatment surface;
    registering data representing the treatment surface and the treatment location at an interventional imaging device;
    positioning the interventional device to face the treatment surface;
    determining a first direction perpendicular to a normal to a local tangent plane of the treatment surface of the tissue, the local tangent plane being located at the treatment location on the treatment surface;
    imaging, by the interventional medical imaging device, the tissue at the treatment location and at least a neighbouring part of the interventional device from the first direction to obtain first interventional image data;
    enhancing, using the first interventional image data, a position of the interventional device in a direction of the normal and in a second direction perpendicular to the normal and perpendicular to the first direction.

2. The method according to clause 1, further comprising:
    imaging, by the interventional medical imaging device, the treatment location and at least the neighbouring part of the interventional device from a third direction having a component in the first direction to obtain a second interventional image data, enhancing, using the second interventional image data, a position of the interventional device in the first direction.
3. The method according to clause 1 or 2, wherein the enhancing, using the first interventional image data, the position of the interventional device in the direction of the normal and in the second direction perpendicular to the normal and perpendicular to the first direction, comprises fusing a display of the treatment point and the first interventional image data.
4. The method according to any of the preceding clauses, wherein the enhancing, using the first interventional image data, the position of the interventional device in the direction of the normal and in the second direction perpendicular to the normal and perpendicular to the first direction, comprises sending instructions to the interventional device to adjust a position of the interventional device.
5. The method according to any of the preceding clauses, further comprising:
providing an absorption model expressing a load by the interventional imaging device onto the body of the patient;
calculating, using the absorption model, a load by the interventional imaging device onto the body of the patient as a function of a direction of imaging of the interventional imaging device; and
adjusting at least one of the first direction and third direction based on the calculated load.
6. The method according to any of the preceding clauses, wherein the normal to the local tangent plane of the treatment surface is determined by selecting a vertex on the treatment surface and determining the normal to the local tangent plane from a normal vertex at the selected vertex.
7. The method according to any of the preceding clauses, wherein an angle between the third direction and the first direction is between 15 degrees and 90 degrees, more preferably substantially 45 degrees.
8. The method according to any of the preceding clauses, wherein the interventional medical imaging device is set to image in the third direction by rotating the interventional medical imaging device, after taking the first interventional image, along a main axis of rotation of the interventional imaging device, by at least 15 degrees, preferably by substantially 45 degrees.
9. The method according to any of the preceding clauses, comprising:
selecting, in the diagnostic medical imaging data, a cross sectional plane defined by the normal to the local tangent plane of the treatment surface and the second direction, and
displaying a resulting diagnostic medical imaging data of the cross sectional plane with a displaying of the interventional medical imaging data.
10. The method according to any of the preceding clauses, comprising:
recognizing, in the diagnostic medical imaging data, an organ other than the tissue at which the treatment surface is defined,
calculating, for each point in the segmented medical image data, a distance from the organ to the point in the segmented medical image data, and
wherein the defining the treatment location comprises taking account of the calculated distance from the organ to the point in the segmented medical image data.
11. The method according to clause 10, wherein the taking account of the calculated distance comprises maintaining a predetermined minimum distance between the organ and the treatment location.
12. The method according to any of the preceding clauses, further comprising:
copying the treatment location from the diagnostic medical image data to the interventional medical image data, and highlighting, in the interventional medical image data as obtained by the interventional imaging device, the copied treatment location.
13. The method according to any of the preceding clauses, further comprising:
providing a geometric outline model of the interventional device; determining in the diagnostic medical image data, an available space facing the treatment surface,
modelling, at the treatment location in the diagnostic medical image data, the geometric outline model of the interventional device in the available space, and
confirming the treatment location if the geometric outline model of the interventional device fits in the available space at the treatment location.
14. The method according clause 13, further comprising:
selecting, based on the determined available space, an interventional device from a plurality of available interventional devices, the selected interventional device fitting in the determined available space.
15. A data processing device for connection to a diagnostic medical imaging device and a an interventional medical imaging device, the data processing device being provided with program instructions for making the data processing device perform the steps of:
receiving, from the diagnostic medical imaging device, diagnostic medical image data representing a diagnostic medical image of the tissue of the patient;
segmenting, using an image segmentation criterion, in the diagnostic medical image data a diseased area image data representing a diseased area of the tissue;
defining, in the segmented diagnostic medical image data, a treatment surface of the tissue;
projecting the diseased area, represented by the diseased area image data, onto the treatment surface;
defining a treatment location on the treatment surface, the treatment location being in, out or at a boundary of the diseased area projected onto the treatment surface;
registering data representing the treatment surface and the treatment location at an interventional imaging device;
providing instructions for positioning the interventional device to face the treatment surface;
determining a first direction perpendicular to a normal to a local tangent plane of the treatment surface of the tissue, the local tangent plane being located at the treatment location on the treatment surface;
providing instructions for imaging, by the interventional medical imaging device, the tissue at the treatment location and at least a neighbouring part of the interventional device from the first direction to obtain first interventional image data so as to enable enhancing, using the first interventional image data, a position of the interventional device in a direction of the normal and in a second direction perpendicular to the normal and perpendicular to the first direction.

16. A software program product comprising program instructions configured to, when loaded into a data processing device, make the data processing device perform the steps of
receiving, from the diagnostic medical imaging device, diagnostic medical image data representing a diagnostic medical image of the tissue of a patient;
segmenting, using an image segmentation criterion, in the diagnostic medical image data a diseased area image data representing a diseased area of the tissue;
defining, in the segmented diagnostic medical image data, a treatment surface of the tissue;
projecting the diseased area, represented by the diseased area image data, onto the treatment surface;
defining a treatment location on the treatment surface, the treatment location being in, out or at a boundary of the diseased area projected onto the treatment surface;
registering data representative of the treatment surface and the treatment location at an interventional imaging device;
positioning the interventional device to face the treatment surface;
determining a first direction perpendicular to a normal to a local tangent plane of the treatment surface of the tissue, the local tangent plane being located at the treatment location on the treatment surface;
providing instructions to the interventional medical imaging device for imaging, by the interventional medical imaging device, the tissue at the treatment location and at least a neighbouring part of the interventional device from the first direction to obtain first interventional image data so as to enable enhancing, using the first interventional image data, a position of the interventional device in a direction of the normal and in a second direction perpendicular to the normal and perpendicular to the first direction.

The invention claimed is:

1. A method of verifying a position of an interventional device at a treatment location in a tissue of a patient, the method comprising:
receiving from a diagnostic medical imaging device, diagnostic medical image data representing a diagnostic medical image of the tissue of the patient;
segmenting, using an image segmentation criterion, in the diagnostic medical image data a diseased area image data representing a diseased area of the tissue;
defining, in the segmented diagnostic medical image data, a treatment surface of the tissue, the treatment surface being curved and extending in a 3 dimensional space, the treatment surface forming a surface on or in the tissue of the patient;
projecting the diseased area, represented by the diseased area image data, onto the treatment surface;
defining a treatment location on the treatment surface, the treatment location being in, out or at a boundary of the diseased area projected onto the treatment surface, the treatment location being on or in the tissue of the patient;
registering data representing the treatment surface and the treatment location at an interventional imaging device;
determining a local tangent plane, the local tangent plane being tangent to the curved treatment surface at the treatment location on the treatment surface on or in the tissue of the patient, wherein the treatment location defines a point of treatment by injection or by placement of a pacemaker electrode on the treatment surface, the local tangent plane being tangential to the curved treatment surface at the point of treatment projected on the treatment surface;
determining a first direction perpendicular to a normal to the local tangent plane of the treatment surface of the tissue, the local tangent plane being located at the treatment location on the treatment surface on or in the tissue of the patient, the normal to the local tangent plane being normal to the treatment surface at the treatment location;
after the interventional device has been positioned to face the treatment location on the treatment surface, performing the steps of:
imaging, by the interventional medical imaging device, the tissue at the treatment location and at least a neighbouring part of the interventional device to obtain first interventional image data from the first direction; and
enhancing, using the first interventional image data, a position of the interventional device in a direction of the normal and in a second direction perpendicular to the normal and perpendicular to the first direction by guiding the interventional device in the patient or by displaying information enabling to verify or adjust the position of the interventional device, the normal to the local tangent plane being normal to the treatment surface at the treatment location,
imaging, by the interventional medical imaging device, the treatment location and at least the neighbouring part of the interventional device to obtain a second interventional image data from a third direction, the third direction having a component parallel to the first direction, and
enhancing, using the second interventional image data, a position of the interventional device in the first direction by guiding the interventional device in the patient or by displaying information enabling to verify or adjust the position of the interventional device in the first direction.

2. The method according to claim 1, wherein the enhancing, using the first interventional image data, the position of the interventional device in the direction of the normal and in the second direction perpendicular to the normal and perpendicular to the first direction, comprises fusing a display of the treatment point and the first interventional image data.

3. The method according to claim 1, wherein the enhancing, using the first interventional image data, the position of the interventional device in the direction of the normal and in the second direction perpendicular to the normal and perpendicular to the first direction, comprises sending instructions to the interventional device to adjust the position of the interventional device.

4. The method according to claim 1, wherein the normal to the local tangent plane of the treatment surface is determined by selecting a vertex on the treatment surface and determining the normal to the local tangent plane from a normal vertex at the selected vertex.

5. The method according to claim 1, wherein an angle between the third direction and the first direction is between 15 degrees and 90 degrees.

6. The method according to claim 1, wherein the interventional medical imaging device is set to image in the third direction by rotating the interventional medical imaging device, after taking the first interventional image, along a main axis of rotation of the interventional imaging device, by between 15 degrees and 90 degrees.

7. The method according to claim 1, comprising:
selecting, in the diagnostic medical imaging data, a cross sectional plane defined by the normal to the local tangent plane of the treatment surface and the second direction, and
displaying a resulting diagnostic medical imaging data of the cross sectional plane with a displaying of the interventional medical imaging data.

8. The method according to claim 1, further comprising:
providing an absorption model expressing a load by the interventional imaging device onto the body of the patient;
calculating, using the absorption model, the load by the interventional imaging device onto the body of the patient as a function of a direction of imaging of the interventional imaging device; and
adjusting at least one of the first direction and third direction based on the calculated load.

9. The method according to claim 1, comprising:
recognizing, in the diagnostic medical imaging data, an organ other than the tissue at which the treatment surface is defined,
calculating, for each point in the segmented medical image data, a distance from the organ to the point in the segmented medical image data, and
wherein the defining the treatment location is based on the calculated distance from the organ to the point in the segmented medical image data.

10. The method according to claim 9, wherein the defining the treatment location comprises maintaining a predetermined minimum distance between the organ and the treatment location.

11. The method according to claim 1, further comprising:
copying the treatment location from the diagnostic medical image data to the interventional medical image data, and highlighting, in the interventional medical image data as obtained by the interventional imaging device, the copied treatment location.

12. The method according to claim 1, further comprising:
providing a geometric outline model of the interventional device;
determining in the diagnostic medical image data, an available space facing the treatment surface,
modelling, at the treatment location in the diagnostic medical image data, the geometric outline model of the interventional device in the available space, and
confirming the treatment location if the geometric outline model of the interventional device fits in the available space at the treatment location.

13. The method according claim 12, further comprising:
selecting, based on the determined available space, an interventional device from a plurality of available interventional devices, the selected interventional device fitting in the determined available space.

14. The method according to claim 1, comprising:
segmenting, in the diagnostic medical imaging data, a cavity;
segmenting, in the diagnostic medical imaging data, a blood vessel which directly connects to the cavity; and
defining the treatment surface as an overlap of a cross sectional surface of the segmented blood vessel and a surface of the cavity.

15. The method according to claim 1, wherein an angle between the third direction and the first direction is between 30 and 60 degrees.

16. The method according to claim 1, wherein the interventional medical imaging device is set to image in the third direction by rotating the interventional medical imaging device, after taking the first interventional image, along a main axis of rotation of the interventional imaging device, by between 30 and 60 degrees.

17. The method according to claim 1, wherein an angle between the third direction and the first direction is substantially 45 degrees.

18. The method according to claim 1, wherein the interventional medical imaging device is set to image in the third direction by rotating the interventional medical imaging device, after taking the first interventional image, along a main axis of rotation of the interventional imaging device, by substantially 45 degrees.

19. The method according to claim 1, wherein the treatment surface of the tissue of the patient is on or in an internal or external surface of an organ of the patient.

20. A computer configured to connect to a diagnostic medical imaging device and an interventional medical imaging device, the computer being provided with program instructions that make the computer:
receive, from the diagnostic medical imaging device, diagnostic medical image data representing a diagnostic medical image of the tissue of the patient;
segment, using an image segmentation criterion, in the diagnostic medical image data a diseased area image data representing a diseased area of the tissue;
define, in the segmented diagnostic medical image data, a treatment surface of the tissue, the treatment surface being curved and extending in a 3 dimensional space, the treatment surface forming a surface on or in the tissue of the patient;
project the diseased area, represented by the diseased area image data, onto the treatment surface;
define a treatment location on the treatment surface, the treatment location being in, out or at a boundary of the diseased area projected onto the treatment surface, the treatment location being on or in the tissue of the patient;
register data representing the treatment surface and the treatment location at an interventional imaging device;
provide instructions for positioning the interventional device to face the treatment surface;
determine a local tangent plane, the local tangent plane being tangent to the curved treatment surface at the treatment location on the treatment surface on or in the tissue of the patient, wherein the treatment location defines a point of treatment by injection or by placement of a pacemaker electrode on the treatment surface, the local tangent plane being tangential to the curved treatment surface at the point of treatment projected on the treatment surface;
determine a first direction perpendicular to a normal to a local tangent plane of the treatment surface of the tissue, the local tangent plane being located at the treatment location on the treatment surface on or in the tissue of the patient, the normal to the local tangent plane being normal to the treatment surface at the treatment location;
provide instructions to image, by the interventional medical imaging device, the tissue at the treatment location and at least a neighbouring part of the interventional device to obtain first interventional image data from the first direction
enhance, using the first interventional image data, a position of the interventional device in a direction of the normal and in a second direction perpendicular to the normal and perpendicular to the first direction by guiding the interventional device in the patient or by displaying information enabling to verify or adjust the position of the interventional device in the direction of the normal and/or in the second direction perpendicular to the normal and perpendicular to the first direction, provide instructions for imaging, by the interventional medical imaging device, the treatment location and at least the neighbouring part of the interventional device to obtain a second interventional image data from a third direction, the third direction having a component parallel to the first direction, and enhance, using the second interventional image data, a position of the interventional device in the first direction by guiding the interventional device in the patient or by displaying information enabling to verify or adjust the position of the interventional device in the first direction.

21. The computer according to claim 20, wherein the step of enhancing, using the first interventional image data, the position of the position of the interventional device in the direction of the normal and in the second direction perpendicular to the normal and perpendicular to the first direction, comprises fusing a display of the treatment point and the first interventional image data.

22. The computer according to claim 20, wherein the step of enhancing, using the first interventional image data, the position of the interventional device in the direction of the normal and in the second direction perpendicular to the normal and perpendicular to the first direction, comprises sending instructions to the interventional device to adjust the position of the interventional device.

23. The computer according to claim 20, wherein the normal to the local tangent plane of the treatment surface is determined by selecting a vertex on the treatment surface and determining the normal to the local tangent plane from a normal vertex at the selected vertex.

24. The computer according to claim 20, wherein an angle between the third direction and the first direction is between 15 degrees and 90 degrees, preferably between 30 and 60 degrees, more preferably substantially 45 degrees.

25. The computer according to claim 20, being configured to set the interventional medical imaging device to image in the third direction by rotating the interventional medical imaging device, after taking the first interventional image, along a main axis of rotation of the interventional imaging device, by between 15 degrees and 90 degrees, preferably between 30 and 60 degrees, more preferably by substantially 45 degrees.

26. The computer according to claim 20, being configured to:
select, in the diagnostic medical imaging data, a cross sectional plane defined by the normal to the local tangent plane of the treatment surface and the second direction, and
provide instructions to display a resulting diagnostic medical imaging data of the cross sectional plane with a displaying of the interventional medical imaging data.

27. The computer according to claim 20, further being configured to:
provide an absorption model expressing a load by the interventional imaging device onto the body of the patient;
calculate, using the absorption model, the load by the interventional imaging device onto the body of the patient as a function of a direction of imaging of the interventional imaging device; and
adjust at least one of the first direction and third direction based on the calculated load.

28. The computer according to claim 20, being configured to:
recognize, in the diagnostic medical imaging data, an organ other than the tissue at which the treatment surface is defined,
calculate, for each point in the segmented medical image data, a distance from the organ to the point in the segmented medical image data, and
wherein the define the treatment location is based on the calculated distance from the organ to the point in the segmented medical image data.

29. The computer according to claim 28, wherein the defining the treatment location comprises maintaining a predetermined minimum distance between the organ and the treatment location.

30. The computer according to claim 20, further being configured to:
copy the treatment location from the diagnostic medical image data to the interventional medical image data, and highlighting, in the interventional medical image data as obtained by the interventional imaging device, the copied treatment location.

31. The computer according to claim 20, further being configured to:
provide a geometric outline model of the interventional device;
determine in the diagnostic medical image data, an available space facing the treatment surface,
model, at the treatment location in the diagnostic medical image data, the geometric outline model of the interventional device in the available space, and
confirm the treatment location if the geometric outline model of the interventional device fits in the available space at the treatment location.

32. The computer according claim 31, further being configured to:
select, based on the determined available space, an interventional device from a plurality of available interventional devices, the selected interventional device fitting in the determined available space.

33. The computer according to claim 20, being configured to:
segment, in the diagnostic medical imaging data, a cavity;
segment, in the diagnostic medical imaging data, a blood vessel which directly connects to the cavity; and
define the treatment surface as an overlap of a cross sectional surface of the segmented blood vessel and a surface of the cavity.

34. A system comprising a diagnostic medical imaging device, an interventional medical imaging device, and the computer according to claim 20, the computer being connected with the diagnostic medical imaging device and the interventional medical imaging device.

35. A method comprising operating the computer according to claim 20 to verify a position of an interventional medical imaging device at a treatment location in a tissue of a patient, the computer being connected with a diagnostic medical imaging device and the interventional medical imaging device.

36. The computer according to claim 20, wherein an angle between the third direction and the first direction is between 30 and 60 degrees.

37. The computer according to claim 20, being configured to set the interventional medical imaging device to image in the third direction by rotating the interventional medical imaging device, after taking the first interventional image, along a main axis of rotation of the interventional imaging device, by between 30 and 60 degrees.

38. The computer according to claim 20, wherein an angle between the third direction and the first direction is substantially 45 degrees.

39. The computer according to claim 20, being configured to set the interventional medical imaging device to image in the third direction by rotating the interventional medical imaging device, after taking the first interventional image, along a main axis of rotation of the interventional imaging device, by substantially 45 degrees.

40. The computer according to claim 20, wherein the treatment surface of the tissue of the patient is on or in an internal or external surface of an organ of the patient.

41. A non-transitory computer readable medium comprising program instructions that, when executed by a processor, perform the steps of
- receiving, from the diagnostic medical imaging device, diagnostic medical image data representing a diagnostic medical image of the tissue of a patient;
- segmenting, using an image segmentation criterion, in the diagnostic medical image data a diseased area image data representing a diseased area of the tissue;
- defining, in the segmented diagnostic medical image data, a treatment surface of the tissue, the treatment surface being curved and extending in a 3 dimensional space, the treatment surface forming a surface on or in the tissue of the patient;
- projecting the diseased area, represented by the diseased area image data, onto the treatment surface;
- defining a treatment location on the treatment surface, the treatment location being in, out or at a boundary of the diseased area projected onto the treatment surface, the treatment location being on or in the tissue of the patient;
- registering data representative of the treatment surface and the treatment location at an interventional imaging device;
- positioning the interventional device to face the treatment surface;
- determining a local tangent plane, the local tangent plane being tangent to the curved treatment surface at the treatment location on the treatment surface on or in the tissue of the patient, wherein the treatment location defines a point of treatment by injection or by placement of a pacemaker electrode on the treatment surface, the local tangent plane being tangential to the curved treatment surface at the point of treatment projected on the treatment surface;
- determining a first direction perpendicular to a normal to a local tangent plane of the treatment surface of the tissue, the local tangent plane being located at the treatment location on the treatment surface on or in the tissue of the patient, the normal to the local tangent plane being normal to the treatment surface at the treatment location;
- providing instructions to the interventional medical imaging device for imaging, by the interventional medical imaging device, the tissue at the treatment location and at least a neighbouring part of the interventional device to obtain first interventional image data from the first direction; and
- enhancing, using the first interventional image data, a position of the interventional device in a direction of the normal and in a second direction perpendicular to the normal and perpendicular to the first direction by guiding the interventional device in the patient or by displaying information enabling to verify or adjust the position of the interventional device in the direction of the normal and/or in the second direction perpendicular to the normal and perpendicular to the first direction,
- imaging, by the interventional medical imaging device, the treatment location and at least the neighbouring part of the interventional device to obtain a second interventional image data from a third direction, the third direction having a component parallel to the first direction, and
- enhancing, using the second interventional image data, a position of the interventional device in the first direction by guiding the interventional device in the patient or by displaying information enabling to verify or adjust the position of the interventional device in the first direction.

* * * * *